United States Patent [19]

Forgione et al.

[11] Patent Number: 4,710,542
[45] Date of Patent: Dec. 1, 1987

[54] ALKYLCARBAMYLMETHYLATED AMINO-TRIAZINE CROSSLINKING AGENTS AND CURABLE COMPOSITIONS CONTAINING THE SAME

[75] Inventors: Peter S. Forgione; Balwant Singh, both of Stamford, Conn.

[73] Assignee: American Cyanamid Company, Stamford, Conn.

[21] Appl. No.: 864,627

[22] Filed: May 16, 1986

[51] Int. Cl.$^4$ .............................................. C08L 75/00
[52] U.S. Cl. .................................... 525/127; 525/415; 525/424; 525/438; 525/440; 525/443; 525/456; 525/528; 428/416; 428/425.8; 428/458; 428/460; 428/461
[58] Field of Search ............... 525/127, 415, 424, 440, 525/443, 438, 456, 528; 428/416, 425.8, 458, 460, 461

[56] References Cited

U.S. PATENT DOCUMENTS

| | | | |
|---|---|---|---|
| 3,573,301 | 3/1976 | Winter | 528/73 X |
| 4,384,102 | 5/1983 | Rasshofer et al. | 528/73 |
| 4,533,716 | 8/1985 | Okoshi et al. | 528/73 |

*Primary Examiner*—Theodore E. Pertilla

[57] ABSTRACT

Novel alkylcarbamylmethyl aminotriazines self-cure and also function as crosslinkers for compounds containing active hydrogen groups. When the active hydrogen-containing compounds are hydroxylated polymers, coatings are provided with exceptional resistance to detergent and salt-spray exposure and improved abrasion resistance. The novel aminotriazines also can be combined with fillers as binders which when cured provide shaped articles of manufacture, such as insulation and foundry core molds.

8 Claims, No Drawings

ALKYLCARBAMYLMETHYLATED AMINO-TRIAZINE CROSSLINKING AGENTS AND CURABLE COMPOSITIONS CONTAINING THE SAME

The present invention relates to curing agents, to curable compositions and to methods of making and using them. More particularly, the present invention relates to novel curing agents comprising alkylcarbamylmethylaminotriazines and to curable compositions comprising an active hydrogen-containing material, a novel alkylcarbamylmethylaminotriazine and a cure catalyst. Coatings cured from the compositions have exceptional resistance to detergent and salt spray exposure, making them well adapted for use in powder coatings, coil coatings and can coatings. The new compositions can be used with filler to provide shaped articles of manufacture with superior properties.

BACKGROUND OF THE INVENTION

Curable compositions containing aminotriazine compounds are known in the art. As is shown in Koral et al., U.S. Pat. No. 3,661,819, for example, a preferred family of aminotriazine curing agents comprises (i) a triaminotriazine compound of the formula:

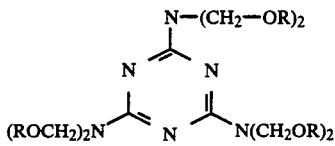

which will be depicted hereinafter as $C_3N_6(CH_2OR)_6$; or (ii) a benzoguanamine compound of the formula:

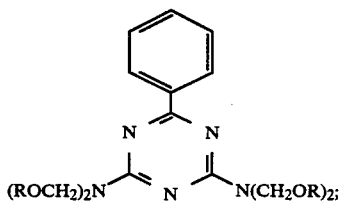

which will be depicted hereinafter as $C_3N_5(C_6H_5)(CH_2OR)_4$ wherein R is hydrogen or alkyl of from 1 to 12 carbon atoms. It is also known to use oligomers of such compounds, which are low molecular weight condensation products containing for example two, three or four triazine rings, joined by —CH$_2$OCH$_2$— linkages, as well as mixtures of any of the foregoing. These are used to cure active hydrogen-containing materials, especially polymers which contain carboxyl groups, alcoholic hydroxy groups, amide groups and groups convertible to such groups, such as methylol groups. When such curable compositions are applied to substrates as coatings and then cured, excellent hardness, impact resistance, light stability and solvent resistance is imparted to the articles. The compositions can also be formulated with fillers and/or reinforcements such as particulate and fibrous mineral and organic materials, such as cellulose, wood, glass, graphite, textiles, silica, asbestos, wollerstonite, and the like to produce insulation, foundry molds and the like which have superior properties and show a reduced tendency to emit formaldehyde during use.

As is described in German Patent OL No. 2,005,693 (1971) (Chemical Abstracts 76:P 34864 a (1972)), when triaminotriazines of the general formula (i) above are reacted with arylurethanes, such as phenyl urethane, there are produced reaction products of the typical formula $C_3N_6(CH_2—NH—COOC_6H_5)_6$, and when these are reacted with polymers containing hydroxyl groups such as acrylics and polyesters, crosslinking occurs with the development of colorless, very hard films, which remain colorless even when the baking time is increased tenfold, to five hours at 100° C. However, subsequent experiments have shown that such coatings, like those crosslinked with the triazines of formulae (i) and (ii) above, are somewhat deficient in detergent resistance, salt spray resistance and adhesion. They also are produced with the liberation of phenol, which causes health and disposal problems, and is economically wasteful.

It has now been discovered that if aminotriazines of general formulae (i) and (ii) are reacted with alkylurethanes (which are well known to be less reactive than the aryl carbamates used in the above-mentioned German Patent), derivatives are formed which are also reactive to crosslink active hydrogen-containing polymers, but the new coatings which are formed have much improved properties (detergent, salt spray, adhesion, color retention) over those of the prior art, particularly the aryl-substituted derivatives of OL No. 2,005,693.

Although it is known, e.g., from Amin et al., Indian J. Chem., 14B, 139–140 (1976), to prepare both aryl and alkyl carbamylmethylated melamines, by the reaction of trimethylolmelamine with n-hexyl carbamate, only the mono-substituted product was produced, and this would not be capable of acting as a crosslinker to introduce two or more urethane groups. Such groups are now believed to be essential to secure all of the advantages of the present invention.

Thus the present invention differs from the state of the art by providing aminotriazine derivatives containing at least two alkylcarbamylmethyl groups and then using them as crosslinkers for active hydrogen-containing materials to provide coatings with exceptional resistance, for example, to detergent and salt-spray exposure, and improved light stability.

SUMMARY OF THE INVENTION

According to the present invention there are provided triazine compounds selected from:
(i) a triaminotriazine compound of the formula $C_3N_6(CH_2OR)_{6-x}(CH_2NHCOOR^1)_x$;
(ii) a benzoguanamine compound of the formula $C_3N_5(C_6H_5)(CH_2OR)_{4-y}(CH_2NHCOOR^1)_y$;
(iii) an oligomer of (i) or of (ii); or
(iv) a mixture of at least two of any of (i), (ii) and (iii), wherein the R groups are, independently, hydrogen or alkyl of from 1 to 12 carbon atoms, the $R^1$ groups are, independently, alkyl of from 1 to 20 carbon atoms, x is in the range of from about 2 to about 6, and y is in the range of from about 2 to about 4.

In preferred embodiments of the invention, x is in the range of from about 2.8 to about 6 and y is in the range of from about 2.2 to about 4. With respect to compound (i) R is lower alkyl, preferably $C_1$–$C_8$ and $R^1$ is methyl, ethyl, n-propyl, i-propyl, butyl, n-octyl, 2-ethylhexyl, n-octadecyl, or a mixture of any of the foregoing. Also preferred are oligomers of (iii)(i) in which R is methyl and $R^1$ is methyl, ethyl, n-propyl, i-propyl, butyl or a mixture of any of the foregoing as well as benzoguanamines (ii) wherein R and $R^1$ are the same as defined above with respect to compound (i).

Also contemplated by the present invention are curable compositions comprising
(a) an active hydrogen-containing material;
(b) a triazine compound selected from
  (i) a triaminotriazine compound of the formula $C_3N_6(CH_2OR)_{6-x}(CH_2NHCOOR^1)_x$;
  (ii) a benzoguanamine compound of the formula $C_3N_5(C_6H_5)(CH_2OR)_{4-y}(CH_2NHCOOR^1)_y$;
  (iii) an oligomer of (i) or of (ii) ; or
  (iv) a mixture of at least two of any of (i), (ii) and (iii), wherein the R groups are, independently, hydrogen or alkyl of from 1 to 12 carbon atoms, the $R^1$ groups are, independently, alkyl of from 1 to 20 carbon atoms, x is in the range of from about 2 to about 6, and y is in the range of from about 2 to about 4; and
(c) a cure catalyst.

In preferred features of this aspect of the invention, the active-hydrogen containing material (a) is a polymeric material containing at least two reactive carboxyl, alcoholic hydroxy, amide or amine groups, or a mixture of such groups, or a group convertible to such groups, preferably a hydroxy-functional acrylic resin or a low molecular weight polyester polyol. Preferably the triazine will be as set forth specifically above, and the cure catalyst will be a metal salt or metal complex comprising tin, especially preferably tetrabutyldiacetoxy stannoxane.

Alternatively, the alkylcarbamylmethyl triazines can be used as a self-crosslinkable material in providing protective and/or decorative coatings.

Also provided by the invention are articles of manufacture comprising substrates protectively coated with a cured composition as defined above and articles of manufacture comprising a cured composition as defined above and a filler, e.g., glass, e.g., glass powder, glass beads, glass fibers or foundry sand.

DETAILED DESCRIPTION OF THE INVENTION

As starting materials to produce the alkylcarbamylmethylated triazines of this invention, there can be used the hydroxymethyl or alkoxymethyl melamines and/or benzoguanamines and oligmers thereof known in the art. Many of the starting materials are commercially available, and can be made by well known procedures. In accordance with the present invention, the starting materials are reacted with alkyl carbamates, such as methyl carbamate and propyl carbamate, which also are well known in this art, in the presence of an acid catalyst.

An idealized reaction equation for the preparation of the new compounds from an alkoxymethylmelamine or a hydroxymethylmelamine is as follows:

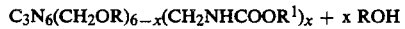

wherein R, $R^1$ and x are as defined above.

The mole ratio of alkyl carbamate is selected to provide the desired degree of substitution. By way of illustration, from 2 to 6 moles can be used. Reaction is typically carried out by heating in the melt or in solution, e.g., in benzene, toluene, xylene, chlorobenzene, dichlorobenzene, e.g., in the presence of catalytic amounts of acid, e.g., para-toluenesulfonic acid, nitric acid, sulfuric acid, and the like, at temperatures between 80° and 150° C., preferably 90°–120° C. Measurement of the quantity of alcohol (ROH) evolved gives an indication of reaction completion. With 6 moles of alkyl carbamate, reaction is usually not 100% complete, unless forced, but a high degree of substitution, x=5-6, is obtained. Analysis by gel permeation chromotography shows that treatment of hexamethoxymethylolmelamine with substantially less than 6 moles of alkyl carbamate gives a product distribution similar to the starting material with degrees of substitution ranging up to 6. Of course, only those compounds wherein at least two carbamylmethyl groups are present are crosslinkers according to this invention, even though residual alkoxymethyl groups can provide crosslinking.

Instead of alkoxymethylmelamines, hydroxymethylmelamines, and the corresponding benzoguanamine analogs and oligomers can be used as starting materials. The products can be recovered by any convenient means after removal of byproduct water or alcohol is complete. Simply cooling to room temperature will leave the product as a residue, and the acid catalyst can be removed by neutralization.

The substituents defined by R and $R^1$ in the formulae above can vary widely in carbon content, and the groups can be straight chain, branched chain and alicyclic. A number of representative compounds will be exemplified in detail hereinafter.

The active hydrogen-containing materials have as the active hydrogen group a group selected from carboxyl, alcoholic hydroxyl, amido, primary amine, secondary amine (including imine), thiol and the like. The active hydrogen-containing materials useful herein are typically film-forming compositions. Illustrative examples of active hydrogen-containing materials are shown in the above-mentioned Koral patent, the above-mentioned German OLS No. 2,055,693, and in Valko, U.S. Pat. No. 4,435,559. Typical polymers are acrylic polymers, polyesters, epoxy resins, and the like, providing that they contain active hydrogen groups.

Especially suitable are polyesters and polyacrylates containing pendant hydroxyl groups as reaction sites. The former are obtained in a known manner by the reaction of polycarboxylic acids with excess quantities of polyhydric alcohols; the latter are obtained by the copolymerization of acrylic or methacrylic acid derivatives with hydroxyl-group-containing derivatives of these acids, such as, for example, the hydroxyalkyl esters, optionally with the simultaneous use of additional vinyl compounds, such as, for example, styrene. Hydroxyl-group-containing polyurethanes can be obtained in known manner by the reaction of polyisocyanates with excess quantities of compounds containing at least two hydroxy groups. Suitable commercially available hydroxy-group-containing polyesters are CYPLEX ® 1473 and CYPLEX ® 1531 from American Cyanamid Company and Cargil Polyester 5776. Suitable hydroxy- functional acrylic resins are available commercially from S. C. Johnson & Son, Inc. under the trademark JONCRYL ®-500. Also suitable for use are a hydroxy-terminated polycaprolactone, as well as the copolymer of 50% styrene, 20% hydroxypropyl methacrylate and 30% butyl acrylate of Example 5 of the above-mentioned German OLS No. 2,055,693 and the polyester of phthalic acid, adipic acid, ethanediol, and trimethylolpropane, with a hydroxy number of 130 and an acid number of 1.5 of Example 6 of the said OLS publication.

As set forth herein, the curable composition includes a cure catalyst. Typically, the cure catalyst is a metal salt and/or complex of a metal such as lead, zinc, iron, tin and manganese, preferably tin. Suitable salts of these metals are, for example acetates, octoates, laurates and naphthanates. Suitable complexes, for example, are tetrabutyldiacetoxy stannoxane, dibutyltin dilaurate, dimethyltin dilaurate or an acetyl acetonate. The cure catalyst is used in amounts effective to accelerate cure at the temperatures employed, e.g., 120°-220° C. For example, the catalyst is used in amounts from about 0.1 to about 2.0 preferably 0.2 to 1% metal by weight (solids) based on the weight of the curable compositions.

It should also be understood that residual ether functional groups can cure with catalysts usually used with amino resins, such as acid catalysts, e.g., nitric acid, sulfuric acid, p-toluenesulfonic acid and the like. This may be advantageous where lower cure temperatures are useful, e.g., when binding fillers or reinforcements, e.g., textiles, cellulose, wood flour, etc. Also useful as heterogenous acidic catalysts are ion exchange resins in the acid form.

In the practice of the invention, the curable compositions can be adapted for use in solvent-based or water based coating compositions. Coating compositions comprising aqueous dispersions are particularly suited to application by electrodeposition. Generally the compositions will contain about 1 to 75 percent by weight of resin and crosslinker combined, and the weight ratio of crosslinker to resin will range from about 5 to about 40 parts to correspondingly from 60 to 95 parts of said resin.

In many instances a pigment composition and various conventional additives such as antioxidants, surface active agents, coupling agents, flow control additives, and the like, can be included. The pigment composition may be of any conventional type, such as, one or more pigments such as iron oxides, lead oxides, strontium chromate, carbon black, titanium dioxide, talc, barium sulfate, cadmium yellow, cadmium red, chromic yellow, or the like.

After deposition on a substrate, such as a steel panel, the coating composition is devolatilized and cured at elevated temperatures by any convenient method such as in baking ovens or with banks of infrared heat lamps. Curing can be obtained at temperatures in the range of from 120° C. to about 300° C., preferably from 150° C. to about 200° C. for from about 30 minutes at the lower temperatures to about 1 minute at the higher temperatures.

Conventional methods can be used to combine the novel aminotriazines herein with fillers and/or reinforcements and to shape them into useful articles by means well known to accomplish these functions with curable aminotriazine resins. Mixing with glass fillers for example and heating provides insulation shapes for pipes, and the like, after curing, and mixing with foundry sand and curing provides core molds for metal casting. These have superior strength compared to the state of the art and appear to be highly advantageous in not evolving formaldehyde during use.

DESCRIPTION OF THE PREFERRED EMBODIMENTS

The following examples illustrate the compounds and compositions of the present invention. They are not to be construed as limiting the claims in any manner. All parts are by weight.

EXAMPLE 1

Reaction Product of 6 Moles of N-Propyl Carbamate With 1 Mole of Hexamethoxymethylmelamine (6-PC)

Hexamethoxymethylmelamine (47.2 g, 0.121 mole, American Cyanamid Co. CYMEL ® 300), n-propylcarbamate (75.0 g, 0.728 mole), and para-toluenesulfonic acid (0.33 g) are stirred at 95° C. in a flask equipped with a vacuum distillation head. During 50 minutes, the pressure is lowered in stages to 50 mm Hg and 21.1 g of methanol (0.659 mole, 91% of theoretical is collected in the distillate receiver. The product in the reaction flask is cooled to near room temperature, where it is a clear, colorless, very viscous liquid. Methylene chloride (100 ml) is added and stirring for one-half hour dissolves the product. The acid catalyst is removed by washing with sodium carbonate solution, followed by drying over potassium carbonate. Rotary vacuum evaporation gives 98.6 g of clear, colorless, nearly solid product. Nuclear magnetic resonance (NMR) analysis shows that the product has at least five (on average) of the methoxy groups replaced by n-propyl carbamate groups:

$$C_3N_6(CH_2OCH_3)_{0-1}(CH_2NHCOOCH_2CH_2CH_3)_{5-6}$$

Gel permeation chromatography shows one large peak for the monomeric compound (>80%) and two smaller peaks corresponding to dimeric (~10%) and trimeric (~3%) oligomers.

COMPARATIVE EXAMPLE 1A

Reaction Product of 6 Moles of Phenyl Carbamate With 1 Mole of Hexamethoxymethylmelamine (6-PhC)

For comparison purposes, the procedure of Example 1 of German OLS No. 2,005,693 is repeated: Hexamethoxymethyl-melamine (300 g, 1 mole) and 822 grams of phenylurethane (6 moles) are dissolved in two liters of chlorobenzene and, after the addition of 4 grams of p-toluenesulfonic acid, are heated with a vertical condenser, with stirring and passage of $CO_2$, until the boiling point of chlorobenzene is reached. The methanol cleavage starts at approximately 90° to 100° C. A mixture of methanol with a small amount of chlorobenzene comes over first. With increasing temperature, the boiling point of chlorobenzene (130° C.) is reached.

The mixture is then evaporated under vacuum, with stirring, to produce a colorless resin with a softening point of 85° to 120° C., which is soluble in all proportions in ethyl acetate. The yield is high. The product is of the formula $C_3N_6(CH_2NHCOOC_6H_5)_6$.

EXAMPLE 2

Reaction Product of 6 Moles of Methyl Carbamate with One Mole of Hexamethoxymethylmelamine (6-MC)

Hexamethoxymethylmelamine (19.5 g, 0.05 mole), excess methyl carbamate (37.6 g, 0.50 mole), and para-toluene-sulfonic acid (0.86 g, 0.005 mole) are stirred at 97° C. in a flask equipped with a distillation head as in Example 1. The reaction mixture changes from a clear, colorless liquid to a white solid and a few ml. of distillate is formed. The reaction mixture is then allowed to cool to room temperature.

A portion, 20.0 g, of the solid product is powdered and vigorously stirred with 100 ml. of water at room temperature for 1¼ hours. Filtration and drying gives 12.3 g of white solid; m.p.=179°–188° C. Infrared spectroscopy shows that at least 90–95% of the methoxy groups have been replaced by carbamate groups.

Purified product, 31.7 g, amounts to 98% of the theoretical yield of hexamethylcarbamylmethylated melamine, a compound of the formula $$C_3N_6(CH_2NHCOOCH_3)_6$$

EXAMPLE 3

Reaction Product of 2 Moles of n-Octadecyl Carbamate With 1 Mole of Hexamethoxymethylmelamine Hexamethoxymethylmelamine (25.0 g, 0.0641 mole), n-octadecyl carbamate (40.1 g, 0.128 mole), and 0.31 g (0.0018 mole) of para-toluenesulfonic acid are stirred at 100° C. in a flask equipped with a vacuum distillation head. During 30 minutes, the pressure is lowered in stages to 50 mm Hg and distillate is collected in the receiver.

At room temperature the product is opaque, white and has the consistency of mayonnaise. Gas chromatographic analysis of a sample of the product dissolved in methyl isobutyl ketone shows practically no unconverted octadecyl carbamate. The formula is, approximately:

$$C_3N_6(CH_2OCH_3)_4(CH_2NCOOC_{18}H_{37}\text{-}n)_2$$

EXAMPLE 4

Reaction Product of 6 Moles of Isopropyl Carbmate With 1 Mole of Hexamethoxymethylmelamine Hexamethoxymethylmelamine (18.9 g, 0.0485 mole), isopropyl carbamate (30.0 g, 0.291 mole), and para-toluenesulfonic acid (0.13 g., 0.008 mole) and stirred at 95° C. in a flask equipped with a vacuum distillation head. During 45 minutes, the pressure is lowered in stages to 50 mm Hg, and 8.46 g of methanol (0.264 mole, 91% of theoretical) is collected in the distillate receiver. The product is dissolved in 75 ml of methylene chloride and the solution is washed with two portions of aqueous 5% sodium carbonate to remove the acid catalyst. The solution is dried over anhydrous potassium carbonate and rotary vacuum evaporated to give 36.8 g of colorless solid (93% yield). The solid is pulverized to white powder; m.p. 101° to 130° C. (clear, colorless melt). The formula is, approximately:

$$C_3H_6(CH_2NHCOOCH(CH_3)_2)_6$$

EXAMPLE 5

Reaction Product of 2 Moles of n-Octyl Carbamate With 1 Mole of Hexamethoxymethylmelamine Hexamethoxymethylmelamine (22.6 g, 0.0579 mole), n-octyl carbamate (20.0 g, 0.116 mole), and para-toluenesulfonic acid (0.19 g, 0.0011 mole) are stirred at 75° C. in a flask equipped with a vacuum distillation head. During 50 minutes, the pressure is lowered in stages to 50 mm Hg, and 3.58 g of methanol (0.112 mole, 96% of theoretical) is collected in the distillate receiver. The product is dissolved in 150 ml of methylene chloride and the solution is washed with two portions of aqueous 5% sodium carbonate to remove the acid catalyst. The solution is dried over anhydrous potassium carbonate and rotary vacuum evaporated to give 37.2 g of almost-clear, colorless, viscous liquid (96% yield of theoretical product). The infrared spectrum is consistent with the expected structure. Gel permeation chromatography shows peaks attributed to mono-, di-, tri-, and higher-substituted products; little oligomeric material is evident. The formula is, approximately:

$$C_3N_6(CH_2OCH_3)_4(CH_2NHCOOC_8H_{17}\text{-}n)_2$$

EXAMPLE 6

Reaction Product of 6 Moles of n-Propyl Carbamate With 1 Mole of Hexamethylolmelamine The general procedure of Example 1 is repeated, substituting the hydroxymethyltriazine: Hexamethylolmelamine (10.0 g, 0.0327 mole), n-propyl carbamate (20.2 g, 0.196 mole), and para-toluenesulfonic acid (0.60 g, 0.0035 mole) are stirred at 95° C. in a flask equipped with a vacuum distillation head. During 30 minutes, the pressure is lowered in stages to 50 mm Hg., and 3.24 g. of distillate (mostly water, 92% of theoretical) is collected in the distillate receiver. At room temperature, the product in the reaction vessel is a gray-white solid. The infrared spectrum shows little or no residual hydroxyl functionality and is similar to the spectrum of authentic hexa-n-propylcarbamylmethylated melamine, made by Example 1. The general formula is, approximately:

$$C_3N_6(CH_2NHCOOC_3H_7\text{-}n)_6$$

EXAMPLE 7

Reaction Product of 3.5 Moles of n-Propyl Carbamate with 1 Mole of Hexamethoxymethylmelamine The general procedure of the preceding Examples is used to react hexamethoxymethylmelamine (167.8 g, 0.430 moles) with 155.1 g, 1.566 moles of n-propyl carbamate. The acid catalyst in this instance is 0.7 g of concentrated nitric acid. The product weighs 254.2 g and contains only 0.1% residual carbamate. It melts at 85°–95° C. A 65% solids solution in xylene remains clear and colorless for 8 weeks. It has the formula, approximately:

$$C_3N_6(CH_2OCH_3)_{2.5}(CH_2NHCOOC_3H_7\text{-}n)_{3.5}$$

EXAMPLE 8

Reaction Product of 3.5 Moles of Methyl Carbamate With 1 Mole of Hexamethoxymethylmelamine The procedure of Example 7 is repeated substituting 1.589 moles of methyl carbamate. The product weighs 241.7 g and melts at 95°–103° C. It has the formula, approximately:

$$C_3N_6(CH_2OCH_3)_{2.5}(CH_2NHCOOCH_3)_{3.5}$$

EXAMPLE 9

Reaction Product of 3.5 Moles of n-Propyl Carbamate With 1 Mole of Hexamethoxymethylmelamine Oligomer The procedure of Example 7 is repeated, substituting an oligomeric triazine (American Cyanamid Co. CYMEL ® 303), $C_3N_6(CH_2OCH_3)_{5.25}$. The catalyst is removed by extracting a xylene solution of the product mixture with sodium carbonate solution. A 75% solution in xylenes remains clear and colorless for more than 6 weeks. The product melts at 74°–80° C. The formula is, approximately:

$$C_3N_6(CH_2OCH_3)_{1.75}(CH_2NHCO_2C_3H_7)_{3.5}$$

EXAMPLE 10

Reaction Product of 4 Moles of n-Propyl Carbamate With 1 Mole of Hexamethoxymethylmelamine Oligomer The procedure of Example 9 is repeated with the higher mole ratio of n-propyl carbamate. The product, 412.2 g, melts at 80°–90° C. At 75% solids in xylenes and methyl isobutyl ketone, the product in solution remains clear and colorless for more than 6 weeks. It has the following approximate formula:

$$C_3N_6(CH_2OCH_3)_{1.25}(CH_2NHCOOC_3H_7\text{-}n)_{4.0}$$

EXAMPLE 11

Reaction Product of 5 Moles of n-Propyl Carbamate With 1 Mole of Hexamethoxymethylmelamine Oligomer The procedure of Example 9 is repeated with a higher mole ratio of n-propyl carbamate. The product, 32.4 g, melts at 80°–92° C. It has the following approximate formula:

$$C_3N_6(CH_2OCH_3)_{0.25}(CH_2NHCOOC_3H_7\text{-}n)_{5.0}$$

EXAMPLE 12

Reaction Product of 4 Moles of n-Propyl Carbamate and 2 Moles of Methyl Carbamate With 1 Mole of Hexamethoxymethylmelamine The general procedure of Example 9 is used at 95° C. The product, 95.8 g, melts at 85°–95° C. The formula is, approximately:

$$C_3N_6(CH_2NH\text{---}CO_2CH_3)_{1.25}(CH_2NHCO_2C_3H_7\text{-}n)_4$$

EXAMPLE 13

Reaction Product of 5.25 Moles of n-Propyl Carbamate With 1 Mole of Hexamethoxymethylmelamine Oligomer The general procedure of Example 9 is used. The product weighs 113.5 g and melts at 90°–100° C. The formula is, approximately:

$$C_3N_6(CH_2OCH_3)_{0.15}(CH_2NHCOOC_3H_7\text{-}n)_{5.1}$$

EXAMPLE 14

Reaction Product of 2.5 Mole of n-Propyl Carbamate and 2.5 Mole of Methyl Carbamate With 1.0 Mole of Hexamethoxymethylmelamine Oligomer The general procedure of Example 9 is used at 110° C. The product weighs 174.5 g and melts at 85°–95° C. The general formula is, approximately:

$$C_3N_6(CH_2OCH_3)_{0.25}(CH_2NH\text{-}CO_2CH_3)_{2.5}(CH_2NHCO_2C_3H_7\text{-}n)_{2.5}$$

EXAMPLE 15

Reaction Product of 3.5 Mole of n-Propyl Carbamate with 1 Mole of (Trimethoxymethyl-Tributoxymethyl) Melamine (Trimethoxymethyl-tributoxymethyl)melamine (CYMEL ® 1133, American Cyanamid Co., 320.3 g, 0.689 mole), n-propyl carbamate (248.3 g, 2.411 mole) and 1.12 g of concentrated nitric acid are stirred and heated in a 100° C. oil bath under a steady stream of nitrogen. Distillate is collected in a dry-ice/isopropanol cooled trap. After 60 minutes, during which vacuum of up to 50 mm Hg is applied, the reaction is stopped. The hot, crude reaction product is dissolved to 30% solids in mixed xylenes (1059 g of xylenes are added) and extracted once with 300 ml of 5% aqueous sodium carbonate solution. The organic layer is then extracted several times with hot deionized water to neutralize the acid and reduce the amount of residual n-propyl carbamate. The organic layer is dried over potassium carbonate (anhydrous) until clear and then stripped under vacuum of a 65% solids content. The product weighs 698.5 grams.

EXAMPLE 16

Reaction Product of 3.5 Mole of Methyl Carbamate with 1 Mole of (Trimethoxymethyl-Tributoxymethyl)Melamine The procedure of Example 15 is repeated, substituting 376.28 g, 0.809 mole of trimethoxymethyl-tributoxymethylmelamine, 212.42 g, 2.832 mole of methyl carbamate and 1.32 g of conc. nitric acid. The product is recovered by the procedure of Example 9.

In the following examples, the alkylcarbamylmethylated triazines of this invention are formulated into curable compositions and evaluated as coatings. For comparison purposes, the phenylcarbamylmethylated triazine of German OLS No. 2,005,693 (Example 1A herein) is also evaluated.

The general method of preparation is as follows:

Thermosetting coatings containing polyols with alkyl and phenylcarbamylmethylated melamines on steel are prepared by mixing high solids solutions of alkylcarbamyl and arylcarbamylmethyl melamines (65% solids in methyl isobutyl ketone or xylene) with a solution of a hydroxyl functional acrylic resin (specifically, JONCRYL ®-500, S. C. Johnson & Son, Inc.; 85% solids in methyl amyl ketone), a solution of a tin catalyst (tetrabutyldiacetoxy stannoxane, TBDSA, 10% solids in methyl isobutyl ketone), and a flow control additive (FC-431, 10% solids in ethyl acetate, 3M Co.). A second series of coatings compositions is prepared as above but with low molecular polyester polyol as backbone resin (specifically, CYPLEX ® 1473, 60% solids in Xylene, American Cyanamid Co.). Both systems are formulated with and without EPON ®-1001, an epoxy resin (10 parts per hundred-phr, as an 85% solids solution in methyl isobutyl ketone - Shell Co.) to assess resistance properties in particular.

The coatings are applied using #40 or #46 WIRECATORS ® by drawdown of resin formulations on 4"×12" BONDERITE ®-100 treated steel panels. The panels, after drawdown, are held for 10 minutes at room temperature and then cured on racks in a temperature controlled oven, at specified temperatures. The coatings prepared are about 1.2±0.2 mils thick and initially tested for solvent resistance by rubbing with a cloth saturated with methyl ethyl ketone (MEK rubs) in accordance with standard testing methods.

Table 1 illustrates a typical charge composition for preparing a coated panel.

TABLE 1

| Material | % Solids | PHR* | Charge (Grams solution) |
|---|---|---|---|
| CYPLEX ® 1475-5 | 65 | 70 | 32.3 |
| Propyl Carbamate Melamine resin | 60 | 20 | 10.0 |
| EPON ®-1001 | 75 | 10 | 4.0 |
| TBDAS cat. | 10 | 1 | 3.0 |
| FC-431 | 10 | 0.13 | 0.4 |

*PHR = parts per hundred resin; final solution 57.8% solids.

Materials 1–5 are stirred until homogeneous, then filtered through a 10 micron felt filter to remove small particles and deaerated.

The properties of the coatings evaluated include:

| Property | Method |
|---|---|
| Forward and Reverse Impact | ASTM D-3281-73 |
| Color | Visual |
| 20° Gloss | Measured on Glossgard II 20°/60° Gossmeter - Neotec Instr. Div., Pacific Scientific |
| Detergent Resistance at 72° C. | ASTM D-2248-73; reapproved 1982; Evaluation of Degree of Blistering of Paints D-714 |
| Blister Classification | Example: F-8 means few small blisters; D-4 means dense large blisters. The smaller the number following the letter, the larger the blister on a scale of 1–10, with 10 meaning no blistering. |

EXAMPLES 17–22

The crosslinker of Example 1 herein, the reaction product of 6 moles of n-propyl carbamate and 1 mole of hexamethoxymethyl melamine (6-PC), is used with a hydroxy-functional polyacrylate and tetrabutyl-diacetoxystannoxane as cure catalyst. For comparison purposes, formulations are made substituting the reaction product of 6 moles of phenyl carbamate with hexamethoxymethyl melamine (6-PhC) of Comparative Example 1A. The formulations used and the properties of the cured films are set forth in Table 2:

TABLE 2

| | Carbamylmethylated Melamine Crosslinked Acrylic Resin | | | | | |
|---|---|---|---|---|---|---|
| Example | 17 | 18 | 19 | 20 | 21 | 22 |
| Composition (parts by weight) | | | | | | |
| Polyacrylate$^a$ | 80 | 70 | 60 | 50 | 80 | 60 |
| 6-PC$^b$ | 20 | 20 | 40 | 40 | 20 | 40 |
| 6-PhC$^c$ | — | — | — | — | — | — |
| Epoxy Resin$^d$ | — | 10 | — | 10 | — | — |
| TBDAS$^e$ | 1 | 1 | 1 | 1 | 1 | 1 |
| Cure Temp., °C. | 180 | 180 | 180 | 180 | 160 | 160 |
| Cure Time, min. | 20 | 20 | 20 | 20 | 30 | 30 |
| Properties | | | | | | |
| MEK wipes | 200+ | 200+ | 200+ | 200+ | 200+ | 200+ |
| Thickness, mils. | 1.2 | 1.1 | 1.0 | 1.0 | 1.2 | 1.1 |
| Forward Impact, | 30 | 10 | 10 | 20 | 20 | — |
| Color | Clr | Clr | Clr | Clr | Clr | Clr |
| 20° Gloss | 97 | 93 | 95 | 93 | 97 | 96 |
| Knoop Hardness | 13.5 | 13 | 16 | 15.8 | 10.8 | 16.2 |
| Detergent Immersion | | | | | | |
| 72 hrs | M8 | 10 | F9 | 10 | M8 | D9 |
| 120 hrs | D8 | 10 | F8 | 10 | M6 | D8 |
| 192 hrs | D8 | D9 | F9 | 10 | D7 | M9 |
| 240 hrs | — | — | — | 10 | — | — |
| 288 hrs | — | — | — | 10 | — | — |
| 408 hrs | — | — | — | 10 | — | — |
| 456 hrs | — | — | — | 10 | — | — |
| 744 hrs | — | — | — | 10 | — | — |
| 912 hrs | — | — | — | 10 | — | — |
| 1100 hrs | — | — | — | 10 | — | — |
| Composition (parts by weight) | | | | | | |
| Polyacrylate$^a$ | 80 | 70 | 60 | 50 | 80 | 60 |
| 6-PC$^b$ | — | — | — | — | — | — |
| 6-PhC$^c$ | 20 | 20 | 40 | 40 | 20 | 40 |
| Epoxy Resin$^d$ | — | 10 | — | 10 | — | — |
| TBDAS$^e$ | 1 | 1 | 1 | 1 | 1 | 1 |
| Cure Temp., °C. | 180 | 180 | 180 | 180 | 160 | 160 |
| Cure Time, min. | 20 | 20 | 20 | 20 | 30 | 30 |
| Properties | | | | | | |
| MEK wipes | — | 200$^m$ | 200+ | 200+ | 200$^m$ | — |
| Thickness, mils. | 1.1 | 0.94 | 0.88 | 0.83 | 1.2 | 1.0 |
| Forward Impact, | — | 20 | 20 | 20 | 10 | — |
| Color | Clr | Yel | Sl. Brn | Yel | Sl. Yel | Clr |
| 20° Gloss | 94 | 97 | 95 | 91 | 92 | 86 |
| Knoop Hardness | 15.3 | 13 | 18 | 17 | 12.4 | 19.4 |
| Detergent Immersion | | | | | | |
| 72 hrs | M6 | 10 | F6 | 10 | VD6 | M8 |
| 120 hrs | D2 | M8 | F8 | 10 | VD4 | M8 |
| 192 hrs | — | D8 | F8 | 10 | — | M8 |

TABLE 2-continued

| | Carbamylmethylated Melamine Crosslinked Acrylic Resin | | | | | |
|---|---|---|---|---|---|---|
| Example | 17 | 18 | 19 | 20 | 21 | 22 |
| 240 hrs | — | — | — | 10 | — | — |
| 288 hrs | — | — | — | 10 | — | — |
| 408 hrs | — | — | — | 10 | — | — |
| 456 hrs | — | — | — | F6 | — | — |
| 744 hrs | — | — | — | F6 | — | — |
| 912 hrs | — | — | — | F6 | — | — |
| 1100 hrs | — | — | — | F6 | — | — |

[a]JONCRYL ® S. C. Johnson & Son, Inc., 85% solids in methylamylketone;
[b]n-propylcarbamylmethyl melamine (Example 1);
[c]phenylcarbamylmethyl melamine (Comp. Ex. 1A);
[d]EPON ® 1001, Shell Polymers Inc.;
[e]Tetrabutyldiacetoxy stannoxane;
[m]marred; and [s]softened

EXAMPLES 23–30

The crosslinkers of Examples 7 and 8 herein (3.5 PC and 3.5 MC) are used to crosslink the hydroxy functional acrylic resin and evaluated in coatings. The formulations used and the properties obtained are set forth in Table 3:

TABLE 3

| | Carbamylmethylated Melamine-Crosslinked Acrylic Resins | | | | | | | |
|---|---|---|---|---|---|---|---|---|
| Example | 23 | 24 | 25 | 26 | 27 | 28 | 29 | 30 |
| Composition (parts by weight) | | | | | | | | |
| Polyacrylate[a] | 80 | 70 | 60 | 50 | 80 | 70 | 60 | 50 |
| 3.5-PC[b] | 20 | 20 | 40 | 40 | — | — | — | — |
| 3.5-MC[c] | — | — | — | — | 20 | 20 | 40 | 40 |
| Epoxy Resin[d] | — | 10 | — | 10 | — | 10 | — | 10 |
| TBDAS[e] | 1 | 1 | 1 | 1 | 1 | 1 | 1 | 1 |
| Cure Temp., °C. | 180 | 180 | 180 | 180 | 160 | 160 | 180 | 180 |
| Cure Time, min. | 20 | 20 | 20 | 20 | 20 | 20 | 20 | 20 |
| Properties | | | | | | | | |
| MEK wipes | 200+ | 200+ | 200+ | 200+ | 200+ | 200[m] | 200+ | 200 |
| Thickness, mils. | 1.0 | 1.1 | 1.2 | 1.1 | 1.0 | 1.0 | 0.95 | 0.96 |
| Forward Impact, | 30 | 5 | 20 | 18.5 | 30 | 15 | 15 | 20 |
| Color | Clr | Clr | Clr | Clr | Clr | Clr | Clr | Clr |
| 20° Gloss | 90 | 95 | 95 | 91 | 97.5 | 99.5 | 101 | 101 |
| Knoop Hardness | 11.8 | 10.4 | 15.4 | 18.5 | 13 | 15 | 16.4 | 17 |
| Detergent Immersion | | | | | | | | |
| 48 hrs | M8 | — | — | — | — | — | — | — |
| 72 hrs | — | 10 | M8 | 10 | M9 | 10 | 10 | 10 |
| 120 hrs | D8 | D8 | M4 | 10 | D6 | 10 | 10 | 10 |
| 192 hrs | — | D8 | D8 | 10 | D8 | 10 | 10 | 10 |
| 240 hrs | — | — | — | 10 | — | M8 | F8 | 10 |
| 288 hrs | — | — | — | 10 | — | — | F8 | 10 |
| 408 hrs | — | — | — | 10 | — | — | M6 | 10 |
| 456 hrs | — | — | — | 10 | — | — | M4 | 10 |
| 744 hrs | — | — | — | 10 | — | — | M4 | 10 |
| 912 hrs | — | — | — | 10 | — | — | M4 | 10 |
| 1100 hrs | — | — | — | 10 | — | — | — | 10 |
| 1400 hrs | — | — | — | 10 | — | — | — | F9 |

[a]See footnote Table 2
[b]3.5 propyl carbamylmethylmelamine (Ex. 7)
[c]3.5 methyl carbamyl methylmelamine (Ex. 8)
[d]See footnote Table 2
[e]See footnote Table 2

EXAMPLES 31–34

The crosslinker of Example 1 herein, the reaction product of 6 moles of n-propyl carbamate and 1 mole of hexamethoxymethylolmelamine (6-PC) is used with a low molecular weight hydroxyfunctional polyester and tetrabutyldiacetoxy stannoxane as cure catalyst. For comparison purposes, formulations are made substituting the reaction product of 6 moles of phenylcarbamate with hexamethoxymethylmelamine (6-PhC) of Comparative Example 1A. The formulations used and the properties of the cured films are set forth in Table 4:

TABLE 4

| | Carbamylmethylated Melamine-Crosslinked Polyester Resin | | | | |
|---|---|---|---|---|---|
| Example | 31 | 32 | 33 | 34 | 31A |
| Composition (parts by weight) | | | | | |
| Polyester[a] | 80 | 70 | 60 | 50 | 80 |
| 6-PC[b] | 20 | 20 | 40 | 40 | — |
| 6-PhC[c] | — | — | — | — | 20 |
| Epoxy Resin[d] | — | 10 | — | 10 | — |
| TBDAS[e] | 1 | 1 | 1 | 1 | 1 |
| Cure Temp., °C. | 180 | 180 | 180 | 180 | 180 |
| Cure Time, min. | 20 | 20 | 20 | 20 | 20 |
| Properties | | | | | |
| MEK wipes | 200[s] | 200+ | 200 | 200+ | 200[s] |
| Thickness, mils. | .98 | 1.0 | .90 | 1.0 | .92 |
| Reverse impact, | 160 | — | 40 | — | 160 |
| Forward Impact, | 160 | — | 70 | — | 160 |
| Color | Clr | Clr | Clr | Clr | Clr/Yel |
| 20° Gloss | 99 | 102 | 104 | 102 | 92 |
| Knoop Hardness | 15.4 | 18.8 | 19.5 | 18.8 | 14.6 |
| Detergent Immersion | | | | | |

TABLE 4-continued

Carbamylmethylated Melamine-Crosslinked Polyester Resin

| | | | | | |
|---|---|---|---|---|---|
| 48 hrs | — | 10 | — | 10 | — |
| 72 hrs | 10 | — | 10 | — | 10 |
| 96 hrs | 10 | — | 10 | — | M8 |
| 168 hrs | — | 10 | 10 | 10 | — |
| 216 hrs | M6 | 10 | F8 | 10 | D4 |
| 336 hrs | — | M8 | — | 10 | — |
| 398 hrs | M2 | — | M4 | — | — |
| 504 hrs | — | D4–6 | M2 | 10 | — |
| 652 hrs | — | — | — | F8 | — |

| Example | 32A | 33A | 34A | 34B | 34C |
|---|---|---|---|---|---|
| Composition (parts by weight) | | | | | |
| Polyester$^a$ | 70 | 60 | 50 | 80 | 60 |
| 6-PC$^b$ | — | — | — | — | — |
| 6-PhC$^c$ | 20 | 40 | 40 | 40 | 40 |
| Epoxy Resin$^d$ | 10 | — | 10 | — | — |
| TBDAS$^e$ | 1 | 1 | 1 | 1 | 1 |
| Cure Temp., °C. | 180 | 180 | 180 | 160 | 160 |
| Cure Time, min. | 20 | 20 | 20 | 30 | 30 |
| Properties | | | | | |
| MEK wipes | — | 200 | 200 | 200 | 200$^m$ |
| Thickness, mils. | 1.1 | .85 | .85 | .95 | .65 |
| Reverse impact, | — | 140 | 30 | 160 | 160 |
| Forward Impact, | — | 150 | 70 | 160 | 160 |
| Color | Clr | Yel | SlYel | Clr | Clr |
| 20° Gloss | 106 | 107 | 105 | 98 | 101 |
| Knoop Hardness | 19.1 | 21 | 22.5 | 16.2 | 21 |
| Detergent Immersion | | | | | |
| 48 hrs | — | — | — | — | — |
| 72 hrs | 10 | M8 | 10 | 10 | F8 |
| 96 hrs | — | D8 | 10 | 10 | M6 |
| 168 hrs | — | — | 10 | — | — |
| 216 hrs | 10 | D4 | F8 | F9 | D8 |
| 336 hrs | — | — | — | — | — |
| 398 hrs | 10 | — | D4 | D2 | D2 |
| 504 hrs | — | — | — | — | — |
| 652 hrs | D8 | — | — | — | — |

$^a$American Cyanamid Co., CYPLEX ® 1473-5
$^{b-}$See footnote above, Table 2.

EXAMPLES 35–44

The crosslinkers of Examples 7 and 8, (3.5-PC and 3.5-MC) are used with the low molecular weight hydroxyfunctional polyester and tetrabutyldiacetoxystannoxane as cure catalyst. The formulations used and the results obtained are set forth in Table 5:

TABLE 5

Carbamylmethylated Melamine-Crosslinked Polyester Resins

| Example | 35 | 36 | 37 | 38 | 39 |
|---|---|---|---|---|---|
| Composition (parts by weight) | | | | | |
| Polyester$^a$ | 80 | 70 | 60 | 50 | 80 |
| 3.5-PC$^b$ | 20 | 20 | 40 | 40 | — |
| 3.5-MC$^c$ | — | — | — | — | 20 |
| Epoxy Resin$^d$ | — | 10 | — | 10 | — |
| TBDAS$^e$ | 1 | 1 | 1 | 1 | 1 |
| Cure Temp., °C. | 180 | 180 | 180 | 180 | 180 |
| Cure Time, min. | 20 | 20 | 20 | 20 | 20 |
| Properties | | | | | |
| MEK wipes | 200$^m$ | 200+ | 200$^s$ | 200+ | 200+ |
| Thickness, mils. | .92 | .9 | .77 | .96 | .88 |
| Reverse impact, | 160 | — | 120 | — | 150 |
| Forward Impact, | 160 | 100 | 120 | 70 | 160 |
| Color | Clr | Clr | Clr | Sl. Yl. | Clr |
| 20° Gloss | 96 | 85 | 95 | 90 | 99 |
| Knoop Hardness | 14.2 | 17.4 | 18.8 | 21 | 14.4 |
| Detergent Immersion | | | | | |
| 48 hrs | 10 | 10 | — | — | — |

TABLE 5-continued

Carbamylmethylated Melamine-Crosslinked Polyester Resins

| | | | | | |
|---|---|---|---|---|---|
| 72 hrs | — | — | 10 | 10 | 10 |
| 96 hrs | — | — | 10 | 10 | M8 |
| 168 hrs | M6 | 10 | — | — | — |
| 216 hrs | D2 | M8 | M6 | 10 | D4 |
| 336 hrs | — | D2 | — | — | — |
| 398 hrs | — | — | D2 | F8 | — |
| 504 hrs | — | — | — | F6 | — |

| Example | 40 | 41 | 42 | 43 | 44 |
|---|---|---|---|---|---|
| Composition (parts by weight) | | | | | |
| Polyester$^a$ | 70 | 60 | 50 | 80 | 60 |
| 3.5-PC$^b$ | — | — | — | — | — |
| 3.5-MC$^c$ | 20 | 40 | 40 | 20 | 40 |
| Epoxy Resin$^d$ | 10 | — | 10 | — | — |
| TBDAS$^e$ | 1 | 1 | 1 | 1 | 1 |
| Cure Temp., °C. | 180 | 180 | 180 | 160 | 160 |
| Cure Time, min. | 20 | 20 | 20 | 30 | 30 |
| Properties | | | | | |
| MEK wipes | 200+ | 200+ | 200+ | — | — |
| Thickness, mils. | 1.2 | .85 | 1.1 | 1.1 | 1.0 |
| Reverse impact, | 50 | 80 | 10 | — | — |
| Forward Impact, | 50 | 80 | 40 | — | — |
| Color | Sl. Yl. | Clr | Sl. Yl. | Clr | Clr |
| 20° Gloss | 101 | 99 | 102 | 101 | 102 |
| Knoop Hardness | 20 | 22.5 | 23.5 | 18 | 17.2 |
| Detergent Immersion | | | | | |
| 48 hrs | — | — | — | — | — |
| 72 hrs | 10 | 10 | 10 | 10 | 10 |
| 96 hrs | 10 | M8 | 10 | 10 | 10 |
| 168 hrs | — | — | — | — | — |
| 216 hrs | 10 | D4 | 10 | F8 | 10 |
| 336 hrs | — | — | — | — | 10 |
| 398 hrs | 10 | — | 10 | M4 | haze |
| 504 hrs | — | — | 10 | — | VD8 |
| 652 hrs | — | — | VF8 | VD2 | — |

$^a$See footnote above, Table 4
$^b$See footnote above, Table 3
$^c$See footnote above, Table 3
$^d$See footnote above
$^e$See footnote above
$^m$See footnote above
$^s$See footnote above A review of the data in the foregoing tables indicates that improved properties are obtained with the alkylcarbamylmethylated melamines of this invention in comparison with the phenylcarbamylmethylated melamine of the prior art. Particularly outstanding with the acrylic and polyester coatings are the excellent detergent resistance properties of the new alkylcarbamylmethylated melamines. For example, both the methyl and propyl carbamylmethylated melamines give over 1100 hours of blister free coatings in a detergent bath when formulated with acrylic polyol and Epon-1001 versus 408 hours for the phenyl system. In the polyester system, the alkylcarbamate system gives 504 hours of blister free coatings versus 398 hours for the phenylcarbamate system in a detergent bath.

EXAMPLES 45–52

Unpigmented coating formulations are prepared by the general procedure described above and cured on steel panels at 177° C. for 6-PC and benzoguanamine resins (CYMEL ® 1123) and at 125° C. for melamine oligomer methoxymethyl (CYMEL ® 303) resins, using hydroxy functional polyesters and 20 min. cure times. In addition to detergent resistance, salt spray resistance and pencil hardness are measured. The formulations used and the results obtained are set forth in Table 6, as follows:

TABLE 6

Carbamylmethylmelamine-Cured Polyesters

| Example | 45 | 46 | 47 | 48 | 49 | 50 | 51 | 52 | 50A | 51A |
|---|---|---|---|---|---|---|---|---|---|---|
| Composition (parts by weight) | | | | | | | | | | |
| Polyester (CYPLEX ® 1473-5) | 60 | 70 | 75 | 80 | 85 | 75 | 70 | 65 | 75 | 75 |
| 6-PC | 40 | 30 | 25 | 20 | 15 | 15 | 20 | 25 | — | — |
| CYMEL ® 303 | — | — | — | — | — | — | — | — | 15 | — |
| CYMEL ® 1123 | — | — | — | — | — | — | — | — | — | 15 |
| EPON ® 1001 | — | — | — | — | — | 10 | 10 | 10 | 10 | 10 |
| TBDAS | 1 | 1 | 1 | 1 | 1 | 1 | 1 | 1 | — | — |
| p-TSA | — | — | — | — | — | — | — | — | .4 | .4 |
| Properties | | | | | | | | | | |
| Pencil hardness | 3H–4H | 2H–3H | 2H–3H | 3H | 2H–3H | 2H–3H | 3H–4H | 4H–5H | 2H–3H | H–2H |
| Knoop hardness | 23 | 16.4 | 16.6 | 17.5 | 16 | 16 | 21.5 | 19.4 | 15.6 | 15.5 |
| Reverse Impact | 60 | 150 | 150 | 160 | 160 | 160 | 160 | 160 | 160 | 150 |
| T-Bond | T5 | T2 | T4 | T3 | T1 | T2 | T4 | T4 | T2 | T4 |
| Detergent Resistance, Blister Code, Hrs. | | | | | | | | | | |
| 48 | F9 | F8 | M9 | M9 | M8 | 10 | 10 | 10 | 10 | 10 |
| 72 | M8 | M8 | M8 | M8 | M8 | 10 | 10 | 10 | 10 | 10 |
| 216 | D7 | D6 | D7 | D7 | D6 | 10 | F9 | 10 | (168-D9) | D7 |
| 384 | D7 | D4 | D6 | D6 | D4 | 10 | D9 | 10 | — | D4 |
| Salt Spray Exposure | | | | | | | | | | |
| Blister Code, 46 Hrs. | 10 | 10 | 10 | 10 | F8 | 10 | 10 | 10 | 10 | 10 |
| Tape Pull, mm | 0 | 1 | 1 | 1 | 0 | 0 | 0 | 0 | 0 | 0 |
| 168 hrs | 10 | 10 | 10 | 10 | 10 | 10 | 10 | 10 | — | 10 |
| mm | 1 | 2 | 2 | 2 | 3 | 0 | 0 | 0 | — | 0 |
| 300 hrs | 10 | 10 | 10 | 10 | 10 | 10 | 10 | 10 | — | 10 |
| mm | 2.5 | 2 | 2.5 | 2 | 4 | 0 | 0 | 0 | — | 0 |
| 468 hrs | 10 | 10 | 10 | 10 | 10 | 10 | 10 | 10 | — | — |
| mm | 4 | 3.5 | 4 | 3.5 | 5 | 0 | 0 | 0 | — | — |
| 1080 hrs | | | | | | 10 | 10 | 10 | D4 | F2 |
| mm | | | | | | 0 | 0 | 0 | 0 | 4 |
| 1440 hrs | | | | | | 10 | 10 | 10 | M4/6 | — |
| mm | | | | | | 0 | 0 | 0 | Striped | — |

EXAMPLES 53–60

Unpigmented coating formulations are prepared by the general procedure described above and cured on steel panels at 177° C. for 6-PC and at 125° C. for the melamine oligomer resin, using a different hydroxy-functional polyester and a 20 min. cure time. The formulations used and the results obtained are set forth in Table 7, as follows:

TABLE 7

Carbamylmethylmelamine-Cured Polyesters

| Example | 53 | 54 | 55 | 56 | 57 | 58 | 59 | 60 | 58A | 58B |
|---|---|---|---|---|---|---|---|---|---|---|
| Composition (parts by weight) | | | | | | | | | | |
| Polyester (CYPLEX ® 1473-5) | 60 | 67 | 70 | 75 | 80 | 75 | 70 | 65 | 75 | 75 |
| 6-PC | 40 | 33 | 30 | 25 | 20 | 15 | 20 | 25 | — | — |
| CYMEL ® 303 | — | — | — | — | — | — | — | — | 25 | 15 |
| EPON ® 1001 | — | — | — | — | — | 10 | 10 | 10 | — | 10 |
| TBDAS | 1 | 1 | 1 | 1 | 1 | 1 | 1 | 1 | — | — |
| p-TSA | — | — | — | — | — | — | — | — | 0.4 | 0.4 |
| Properties | | | | | | | | | | |
| Pencil hardness | 4H | 4H | 4H | 2H–3H | 2H–3H | 3H–4H | 4H | 3H–4H | H–2H | 2H–3H |
| Knoop hardness | 16.6 | 16.4 | 16.4 | 15.2 | 14.2 | 15.4 | 16.6 | 15.5 | 12.6 | 14 |
| Reverse Impact | 40 | 110 | 120 | 160 | 160 | 160 | 160 | 160 | 150 | 130 |
| T-Bond | T4 | T3 | T3 | T3 | T2 | T2 | T3 | T4 | T3 | T5 |
| Detergent Resistance, Blister Code, Hrs. | | | | | | | | | | |
| 48 | F9 | F9 | F9 | M9 | F9 | 10 | 10 | 10 | 10 | F8 |
| 72 | F9 | F8 | F9 | M8 | F9 | 10 | 10 | 10 | F9 | F8 |
| 216 | D6 | D6 | D7 | D8 | D8 | M8 | M9 | F9 | D7 | D6 |
| 384 | M/D7 | D5 | D7 | D7 | D7 | M8 | M/D9 | D9 | D4 | — |
| Salt Spray Exposure | | | | | | | | | | |
| Blister Code, 46 Hrs. | 10 | 10 | 10 | 10 | 10 | 10 | 10 | 10 | 10 | D8 |
| Tape Pull, mm | 0 | 1 | 0 | 2 | 1 | 0 | 0 | 0 | 0 | 4 |
| 168 hrs | 10 | 10 | 10 | 10 | 10 | 10 | 10 | 10 | D9 | — |
| mm | 0 | 2 | 2 | 3 | 2 | 0 | 0 | 0 | 2 | 5 |
| 300 hrs | 10 | 10 | 10 | 10 | 10 | 10 | 10 | 10 | — | — |
| mm | 0 | 2 | 4 | 4 | 4 | 0 | 0 | 0 | 3 | 8 |
| 468 hrs | 10 | 10 | 10 | 10 | 10 | 10 | 10 | 10 | — | — |
| mm | 1 | 4 | 5 | 6 | 6 | 0 | 0 | 0 | 4 | 10 |
| 1080 hrs | — | — | — | — | — | 10 | 10 | 10 | M1 | — |
| mm | — | — | — | — | — | 0 | 0 | 0 | disint. | disint. |

TABLE 7-continued

| | Carbamylmethylmelamine-Cured Polyesters | | | | | | | | | |
|---|---|---|---|---|---|---|---|---|---|---|
| Example | 53 | 54 | 55 | 56 | 57 | 58 | 59 | 60 | 58A | 58B |
| 1440 hrs | — | — | — | — | — | 10 | M/ | 10 | — | — |
| mm | — | — | — | — | — | 1 | 0 | 0 | — | — |

EXAMPLES 61-68

Titanium dioxide pigmented coating formulation are prepared by the general procedure described above and cured on steel panels, using 6-PC and methylolmelamine and methylolbenzoguanamine resins, the latter two as controls. The formulations used and the results obtained are set forth in Table 8 as follows:

TABLE 8

| | TiO$_2$ - Pigmented Cured Coatings | | | | | |
|---|---|---|---|---|---|---|
| Example | 61A | 61 | 62 | 62A | 63A | 63 |
| Composition (parts by weight) | | | | | | |
| JONCRYL ® 500[a] | — | — | 75 | 75 | — | — |
| AROPLAZ 1710 R60[b] | 75 | 75 | — | — | — | — |
| CYMEL ® 1473-5[c] | — | — | — | — | — | — |
| CARGILL 5775[d] | — | — | — | — | 75 | 75 |
| CYMEL ® 303[c] | 25 | — | — | — | 15 | — |
| CYMEL ® 1123[c] | — | — | — | 25 | — | — |
| CYMEL 6-PC[e] | — | 25 | 25 | — | — | 25 |
| EPON ® 1001[f] | — | — | — | — | 10 | — |
| T-12[g] | — | — | — | — | — | — |
| TBDAS[h] | — | 1 | 1 | — | — | 1 |
| p-TSA[i] | 0.4 | — | — | 0.5 | 0.4 | — |
| Cure Temp °C. | 125 | 177 | 177 | 177 | 125 | 177 |
| Properties | | | | | | |
| MEK Resist | 200+ | 200+ | 200+ | 200+ | 200 | 200+ |
| Cross-Hatch Adhesion | 3 | 5 | 4 | 5 | 5 | 5 |
| Knoop hardness | 16.6 | 17.5 | 26 | 18 | 10.8 | 21 |
| Reverse Impact | 5 | 30-40 | 5 | 5 | 160 | 40 |
| Film Thickness, mils | 1.2 | 1.1 | 1.1 | 1.3 | 1.3 | 1.2 |
| Detergent Resistance, Blister Code, Hrs. | | | | | | |
| 48 | 10 | 10 | 10 | D8 | 10 | D9 |
| 96 | M/D8/9 | D8 | 10 | D6 | M9 | D9 |
| 124 | — | — | 10 | D9 | M | |
| 148 | — | — | 10 | YD6 | VD9 | VD9 |
| 192 | D8 | D6 | 10 | D4 | peeled | VD9 |
| 288 | VD6 | D4 | D9 | D2 | | VD9 |
| 336 | — | — | D9 | D2 | | VD4 |
| Salt Spray Exposure | | | | | | |
| Blister Code, 46 Hrs. | 10 | 10 | 10 | D9 | 10 | 10 |
| Tape Pull, mm | 1 | 0 | 0 | 0 | 0 | 0.5 |
| 336 hrs | 10 | D8 | 10 | D9 | 10 | 10 |
| mm | 2 | 1.5 | 0 | 3 | 1 | 0 |
| 800 hrs | 10 | D8 | 10 | D9 | 10 | 10 |
| mm | 5 | 5 | 0 | 11 | 8 | 0 |

[a]S. C. Johnson & Son, Inc., hydroxyfunctional polyacrylate;
[b]Spencer Kellog, Div. of Textron, Inc., siliconized polyester;
[c]American Cyanamid Company;
[d]Cargill Co.
[e]Hexa(propylcarbamylmethyl)melamine (Ex. 1);
[f]Shell Chemical Co.;
[g]Dibutyltin dilaurate;
[h]Tetrabutyldiacetoxy stannoxane;
[i]p-toluenesulfonic acid;
NC = no change The foregoing examples show that even without the epoxy resin (EPON ® 1001) additive, the alkylcarbamate melamine systems outperform all state of the art melamine systems, which include the phenyl carbamate, alkoxymethyl and benzoguanamine systems in detergent resistance. The above-mentioned results are unexpected because alkyl urethanes on heating are known to be poorer leaving groups than the phenoxy blocked isocyanate system and therefore they would be expected to give somewhat inferior coating properties. The foregoing examples also show that the alkylcarbamylmethylated melamines of this invention also provide coatings with outstanding salt spray resistance in comparison with other melamine based systems.

It is generally the case also, that the alkylcarbamylmethylated melamines of this invention afford coatings with good color stability. While the phenyl analog gives off white to tan coatings on cure, the alkyl systems are unchanged. In addition, the phenylcarbamate based coatings on exposure to U.V. light change to a much darker color (tan to light brown), while the alkylcarbamate systems change only slightly to a light tan color. Finally, the data show that while outstanding resistance properties and color stability have been obtained with the alkylcarbamate melamines, other important and desirable coatings properties such as Knoop hardness, impact and solvent resistance (MEK rubs+200) have been maintained as is the case with conventional resins.

EXAMPLE 69

The product of Example 1 can be used as a binder for foundry sand. The binder as an acetone solution (e.g., 77 wt. %) containing 1 part/100 of TBDSA catalyst is kneaded with sand and the solvent is vaporized by heating. The amount of binder to sand is preferably 1-5.5 parts to 100 parts of sand. The coated sand is then filled into a core mold and heated at 200°-300° C. for 30 sec. to two minutes. A core having good strength and showing little tendency to give off gases having a strong smell (e.g., formaldehyde) will be obtained.

Instead of sand, glass powder and glass fiber can be substituted, in which case, thermally insulating shapes having good structural integrity will be obtained.

The above-mentioned patents and publications are incorporated herein by reference. Many variations of this invention will suggest themselves to those skilled in this art in light of the above, detailed description. Instead of using n-propylcarbamylmethylated- and methylcarbamylmethylated melamines as curing agents in the formulations of Tables 1-8, the corresponding alkyl (and mixed alkyl) carbamylmethylated melamine and melamine oligomers of Examples 3-16 can be used. Instead of tetrabutyldiacetoxy stannoxane and, dibutyltin dilaurate as cure catalysts, lead octoate, and stannous octoate can be used. Instead of hydroxyfunctional polyesters and polyacrylates, epoxy resins, such as the polyglycidylethers of bisphenol A and the reaction products thereof with amines and ammonia can be used. All such obvious modifications are within the full intended scope of the appended claims.

We claim:

1. A curable composition comprising:
   (a) an active hydrogen-containing material;
   (b) a triazine compound selected from
      (i) a triaminotriazine compound of the formula $C_3N_6(CH_2OR)_{6-x}(CH_2NHCOOR^1)_x$;
      (ii) a benzoguanamine compound of the formula $C_3N_5(C_6H_5)(CH_2OR)_{4-y}(CH_2NHCOOR^1)_y$;
      (iii) an oligomer of (i) or of (ii); or
      (iv) a mixture of at least two of any of (i), (ii) and (iii), wherein the R groups are, independently, hydrogen or alkyl from 1 to 12 carbon atoms, the $R^1$ groups are, independently, alkyl of from 1 to 20 carbon atoms, x is in the range of from about 2 to about 6, and y is in the range of from about 2 to about 4; and
   (c) a cure catalyst.

2. A curable composition as defined in claim 1 wherein the active hydrogen-containing material is a polymeric material containing at least one class of reactive groups selected from carboxyl groups, alcoholic hydroxy groups, amide groups, amine groups or a mixture of any of such groups or a group convertible to any of such groups.

3. A curable composition as defined in claim 2 wherein the active hydrogen-containing material comprises a hydroxy functional acrylic resin or a low molecular weight polyester polyol.

4. A curable composition as defined in claim 1 wherein the triazine compound is a triaminotriazine compound (i) wherein x is in the preferred range of from about 2.8 to about 6.

5. A curable composition as defined in claim 4 wherein, in the triazine compound (i), R is $C_1$-$C_8$ lower alkyl and $R^1$ is methyl, ethyl, n-propyl, butyl, i-propyl, n-octyl, 2-ethylhexyl, n-octadecyl, or a mixture of any of the foregoing.

6. A curable composition as defined in claim 1 wherein the cure catalyst is a metal salt or complex comprising tin.

7. A curable composition as defined in claim 6 wherein the cure catalyst comprises tetrabutyldiacetoxy stannoxane, dibutyltin dilaurate or dimethyltin dilaurate.

8. A substrate protectively coated with a cured composition as defined in claim 1.

* * * * *